United States Patent
Habib et al.

(10) Patent No.: US 8,753,342 B2
(45) Date of Patent: Jun. 17, 2014

(54) METHOD OF USING ELECTROSURGICAL DEVICE FOR RESTRICTING LOSS OF BLOOD DURING SURGERY

(71) Applicant: Emcision Limited, London (GB)

(72) Inventors: Nagy Adly Habib, London (GB); Alan John Sangster, Edinburgh (GB)

(73) Assignee: Emcision Limited, London (GB)

( * ) Notice: Subject to any disclaimer, the term of this patent is extended or adjusted under 35 U.S.C. 154(b) by 0 days.

(21) Appl. No.: 13/849,848

(22) Filed: Mar. 25, 2013

(65) Prior Publication Data

US 2013/0218155 A1 Aug. 22, 2013

Related U.S. Application Data

(63) Continuation of application No. 12/882,612, filed on Sep. 15, 2010, now abandoned, which is a continuation of application No. 10/625,232, filed on Jul. 22, 2003, now abandoned, which is a continuation of application No. 09/762,285, filed as application No. PCT/GB99/02559 on Aug. 4, 1999, now Pat. No. 6,628,990.

(30) Foreign Application Priority Data

Aug. 5, 1998 (GB) .................................. 9817078.0

(51) Int. Cl.
*A61B 18/12* (2006.01)
(52) U.S. Cl.
USPC .......................................................... 606/49
(58) Field of Classification Search
USPC ............ 606/41–49; 607/96, 98–101; 128/898
See application file for complete search history.

(56) References Cited

U.S. PATENT DOCUMENTS

| 4,800,899 A | 1/1989 | Elliot |
| 4,974,587 A | 12/1990 | Turner et al. |
| 5,019,076 A | 5/1991 | Yamanashi et al. |
| 5,370,675 A | 12/1994 | Edwards et al. |
| 5,472,441 A | 12/1995 | Edwards et al. |
| 5,500,012 A | 3/1996 | Brucker et al. |
| 5,599,346 A | 2/1997 | Edwards et al. |
| 5,629,678 A | 5/1997 | Gargano et al. |
| 5,704,352 A | 1/1998 | Tremblay et al. |

(Continued)

FOREIGN PATENT DOCUMENTS

| CN | 1050318 | 4/1991 |
| DE | 197 13 797 | 10/1997 |

(Continued)

OTHER PUBLICATIONS

Wagman LD, et al., Liver Resection Using a Four-Prong Radiofrequency Transaction Device, Am. Surg., Oct. 2009, pp. 991-994, Southeastern Surgical Congress, USA.

(Continued)

*Primary Examiner* — Aaron Roane
(74) *Attorney, Agent, or Firm* — Barbara A. Wrigley; Oppenheimer Wolff & Donnelly LLP

(57) ABSTRACT

A device for generating localized heating in a selected body tissue includes an applicator having a source of microwave radiation and an array of retractable needles arranged so as to extend from one face of the applicator and, in operation, to confine the irradiated microwave energy field emanating from the applicator. The device has application for controlling excessive bleeding from severed tissue during surgical procedures.

21 Claims, 2 Drawing Sheets

(56) References Cited

U.S. PATENT DOCUMENTS

| | | | |
|---|---|---|---|
| 5,833,603 | A | 11/1998 | Kovacs et al. |
| 5,836,906 | A | 11/1998 | Edwards |
| 5,919,191 | A | 7/1999 | Lennox et al. |
| 5,963,132 | A | 10/1999 | Yoakum |
| 6,015,386 | A | 1/2000 | Kensey et al. |
| 6,053,873 | A | 4/2000 | Govari et al. |
| 6,267,760 | B1 | 7/2001 | Swanson |
| 6,287,304 | B1 | 9/2001 | Eggers et al. |
| 6,530,922 | B2 | 3/2003 | Cosman et al. |
| 7,008,421 | B2 | 3/2006 | Daniel et al. |
| 2002/0120260 | A1 | 8/2002 | Morris et al. |
| 2005/0049586 | A1 | 3/2005 | Daniel et al. |

FOREIGN PATENT DOCUMENTS

| | | |
|---|---|---|
| EP | 0073709 | 3/1983 |
| GB | 1095988 | 12/1967 |
| GB | 2119253 | 11/1983 |
| JP | 1990121675 | 5/1990 |
| WO | WO-9639226 | 12/1996 |
| WO | WO98/35619 | 8/1998 |

OTHER PUBLICATIONS

Pai M., et al., Liver Resection With Bipolar Radiofrequency Device: Habib™ 4X, HPB (Oxford), Informa Healthcare, 2008; pp. 256-260. Informa Healthcare, England.

Pai M., et al., Laparscopic Habib™ 4X: a bipolar radiofrequency device for bloodless laparoscopic liver resection, HPB (Oxford), Informa Healthcare, 2008, pp. 261-264. Informa Healthcare, England.

Ayav A., et al., Liver Resection with a New Multiprobe Bipolar Radiofrequency device, Arch. Surg., 2008, pp. 396-401, vol. 143 (No. 4), American Medical Association, USA.

Vávra P. et al., New Treatment Approach in Liver Metastates: hand-assisted laparoscopic radiofrequency liver resection, Rozhl Chir., Oct. 2007, pp. 554-557, vol. 86, No. 10. Nákladem Československé chlruruglcké společnostl, Czech Republic.

Hepatic Resection Using Heat Coagulative Necrosis. First report of successful trisegmentectomy after hypertrophy induction. Langenbecks Arch Surg., Jan. 2007, vol. 392 (1), pp. 95-97, (Epub Nov. 28, 2006, Springer-Verlag, Germany.

Jiao, LR, et al., Laparoscopic Liver Resection Assisted by the Laparoscopic Habib Sealer. Surgery, Nov. 2008, vol. 144 (No. 5), pp. 770-774, (Epub Sep. 19, 2008), Mosby, USA.

El-Gendi, A.M., et al., Repeat Hepatic Resection Using a Radiofrequency-Assisted Technique, Dig. Surg., 2008, vol. 25 (No. 4), pp. 293-299. S. Karger, Switzerland.

Navarra, G., et al., Bloodless Hepatectomy Technique. HPB (Oxford), 2002, vol. 4 (No. 2), pp. 95-97, Informa Healthcare, England.

Ayav A., et al., Bloodless Liver Resection Using Radiofrequency Energy, Dig. Surg., 2007, vol. 24, No. 4, pp. 314-317 (Epub Jul. 27, 2007), S. Karger, Switzerland.

Ayav, A., et al., Results of Major Hepatectomy Without Vascular Clamping Using Radiofrequency-Assisted Technique Compared with Total Vacular Exclusion. Hepatogastroenterology, Apr.-May 2007, vol. 54, No. 75, pp. 806-809. H.G.E. Update Medical Publishing, Greece.

Bachelier, P., et al. Laparoscopic Liver Resection Assisted With Radiofrequency. Am. J. Surg., Apr. 2007, vol. 193 No. 4, pp. 427-430. Excerpta Medica, USA.

Ayav, A., et al., Impact of Radiofrequency Assisted Hepatectomy for Reduction of Tranfusion Requirements. Am. J. Surg., Feb. 2007, vol. 193, No. 3, pp. 143-148. Excerpta Medica, USA.

Ferko, A., et al., A Modified Radiofrequency-Assisted Approach to Right Hemihepatectomy. Eur J. Surg Oncol., Dec. 2006, vol. 32, No. 10, pp. 1209-1211. Elsevier, England.

Jiao, Long R., et al., Radio Frequency Assisted Liver Resection: The Habib's Technique. Adv. Exp. Med. Biol., 2006, vol. 574, pp. 31-37. Kluwer Academic/Plenum Publishers, USA.

Jiao Long R., et al., Radiofrequency Assisted Liver Resection—a Novel Technique. Hepatogestroenterolegy, Nov.-Dec. 2005, vol. 52, No. 66, pp. 1685-1687. H.G.E. Update Medical Publishing, Greece.

Lupo, L., et al., Randomized Clinical Trial of Radiofrequency-Assisted Versus Clamp-Crushing Liver Resection. British Journal of Surgery, 2007, vol. 94, pp. 287-291. John Wiley & Sons Ltd, USA.

Weber, J.C., et al., Laparoscopic Radiofrequency-Assisted Liver Resection. Surg. Endosc., May 2003, vol. 17, No. 5, pp. 834. Springer, Germany.

Habib, N.A., et al., How We Do a Bloodless Partial Splenectomy. Am. J. Surg., Aug. 2003, vol. 186, No. 2, pp. 164-166. Excerpta Medica, USA.

Zacharoulis, D., et al. Hepatectomy Using intraoperative Ultrasound-Guided Radiofrequency Ablation. Int. Surg., Apr.-Jun. 2003, vol. 88, No, 2, pp. 80-82. Minerva Medica, Italy.

Weber, Jean-Christophe, M.D., et al., New Technique For Liver Resection Using Heat Coagulative Necrosis, Annals of Surgery, 2001, vol. 236, No. 5, pp. 560-563. Lippincott Williams & Wilkins, Inc., USA.

Curro, G., et al., Radiofrequency-Assisted Liver Resection in Patients With Hepatocellular Carcinoma and Cirrhosis: Preliminary Results. Transplant Proc., Dec. 2008, vol. 40, No. 10, 3523-3525. Elsevier Science Inc., USA.

Curro, G. et al., Ultrasound-Guided Radiofrequency-Assisted Segmental Liver Resection: A New Technique. Ann. Surg., Aug. 2009, vol. 250, No. 2, pp. 229-233. Lippincott Williams & Wilkins, USA.

Curro G. et al., Radiofrequency-Assisted Liver Resection in Cirrhotic Patients With Hepatocellular Carcinoma. J. Sug. Oncol., Nov. 2008, vol. 98 No. 6, pp. 407-410. Wiley-Liss, USA.

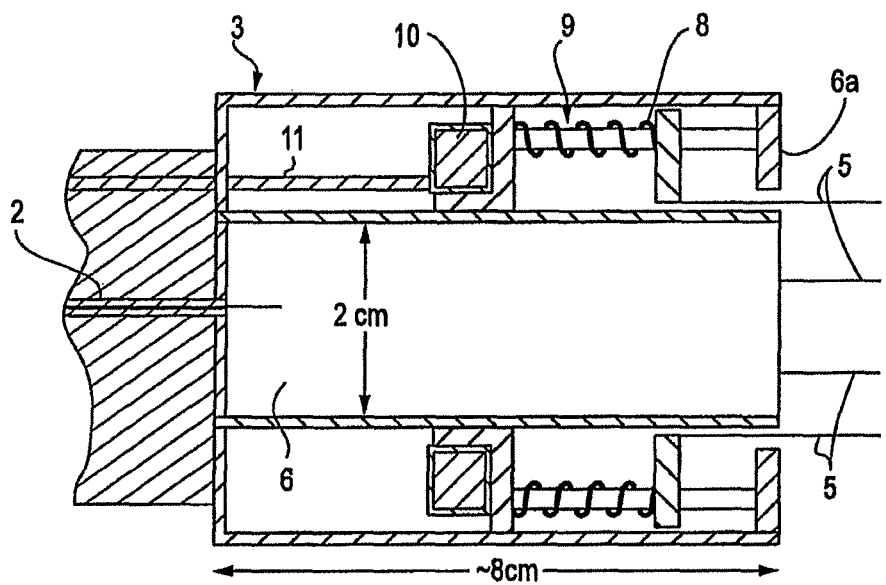
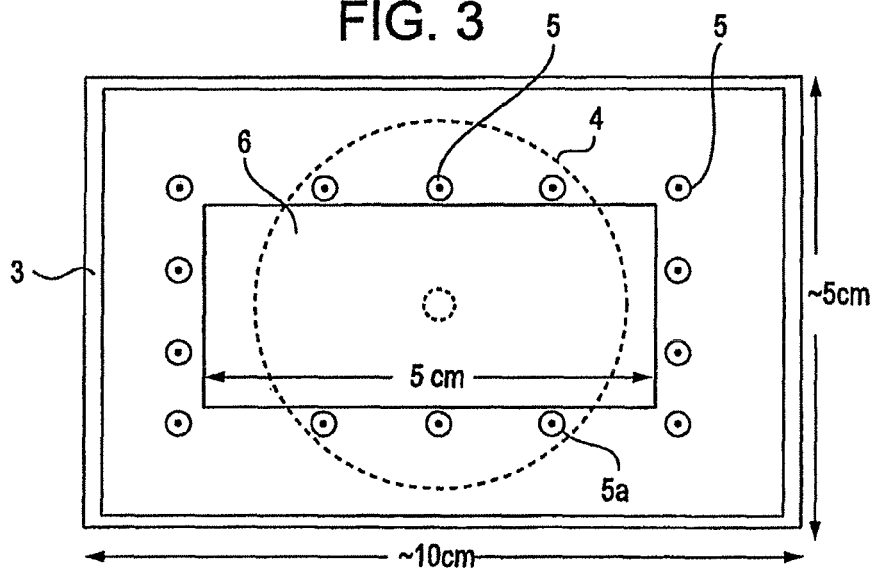

METHOD OF USING ELECTROSURGICAL DEVICE FOR RESTRICTING LOSS OF BLOOD DURING SURGERY

CROSS REFERENCE TO RELATED APPLICATIONS

This application is a continuation of U.S. application Ser. No. 12/882,612, filed on Sep. 15, 2010, which is a continuation of U.S. application Ser. No. 10/625,232 filed Jul. 22, 2003, and which is a continuation of U.S. application Ser. No. 09/762,285, filed Apr. 6, 2001, now U.S. Pat. No. 6,628,990, which is a U.S. national stage application of International patent application No. PCT/GB99/02559, filed Aug. 4, 1999, which claims priority from Great Britain Application No. 9817078.0 filed Aug. 5, 1998, the entireties of which are fully incorporated by reference herein.

FIELD OF THE INVENTION

This invention relates to a device for use in the surgical treatment of human or non-human animals. In particular, it is concerned with a device for use in controlling excessive bleeding from severed tissue during surgical procedures, especially on the patient's liver.

BACKGROUND OF THE INVENTION

It is well known that raising the temperature of body tissue tends to reduce blood flow within the tissue. If the temperature is raised by 20-30.degree. C. above normal, blood flow within the tissue is greatly diminished.

In surgical procedures performed on deep-seated body tissues and organs, e.g. the liver, blood loss from severed tissue can be a serious problem. There is an obvious need for a device which can assist in limiting such blood loss and, as indicated above, this can be achieved by means of the application of heat. Widespread heating can be achieved relatively easily, but this is not desirable. Very, localized heating is required in order to minimize damage to surrounding tissues. In liver surgery, local heating of the liver is ideally required in a tissue volume approximately 5 cm long by 2 cm wide by 4 cm deep; this volume is centered on the planned point of incision. Furthermore, it is important for the local elevation of temperature to be achieved quickly just prior to commencing the surgical procedure.

BRIEF SUMMARY OF THE INVENTION

The present invention aims to provide a device for providing localized heating of a selected region of body tissue prior to surgical incision of that tissue.

According to one aspect of the present invention, there is provided a device for generating localized heating in a selected body tissue, which device comprises an applicator including a source of microwave radiation and an array of retractable needles arranged so as to extend from one face of the applicator and, in operation, to confine the irradiated microwave energy field emanating from the applicator.

The invention also provides the use of the device as defined above for restricting the loss of blood during a surgical procedure on the human or animal body.

According to another aspect of the present invention, there is provided, in the surgical treatment of the human or animal body, a method of controlling excessive bleeding, the method comprising inserting an array of needles into the tissue or organ being treated; and applying microwave energy to the region undergoing treatment for a time sufficient to raise the temperature of said tissue or organ by 20-30 degrees C.

Conveniently, the source of microwave radiation is in the form of a rectangular waveguide whose dimensions correspond to those of the tissue volume which is to be heated. The waveguide is preferably generally rectangular in form, the array of retractable needles being positioned around the periphery of the waveguide.

The device may include a needle advance mechanism including a collar to which the needles are secured; movement of said collar may be actuated by a solenoid mechanism.

In operation of the device, the needles will be advanced from the body of the applicator into the tissue which is to be heated so that the needles function as an extension of the waveguide; in this way, the applicator will direct the required microwave energy into the appropriate tissue volume prior to surgery. When the heating process is completed, the needles are refracted back into the body of the applicator.

Generally, the needles will be disposed mutually parallel; they can conveniently be formed of steel.

Theoretical calculations show that, in order to raise the temperature of body tissues by 30.degree. C., an applicator operating with 100% efficiency would need to deliver about 10 watts of microwave power, assuming that the volume to be heated is 40 cm. For a typical biological tissue such as muscle, this temperature rise would be achieved in approximately 10 minutes. If the source is increased in energy to 500 watt, and if the applicator is assumed to be about 80% efficient, the time taken to achieve this required temperature increase is approximately 15 seconds.

BRIEF DESCRIPTION OF THE DRAWINGS

For a better understanding of the invention, and to show how the same may be carried into effect, reference will now be made, by way of example, to the accompanying drawings, in which:

FIG. 2 is a cross-sectional view of the applicator head of FIG. 1;

FIG. 3 is an end elevational view corresponding to FIGS. 1 and 2.

DETAILED DESCRIPTION OF THE INVENTION

Figure 1:
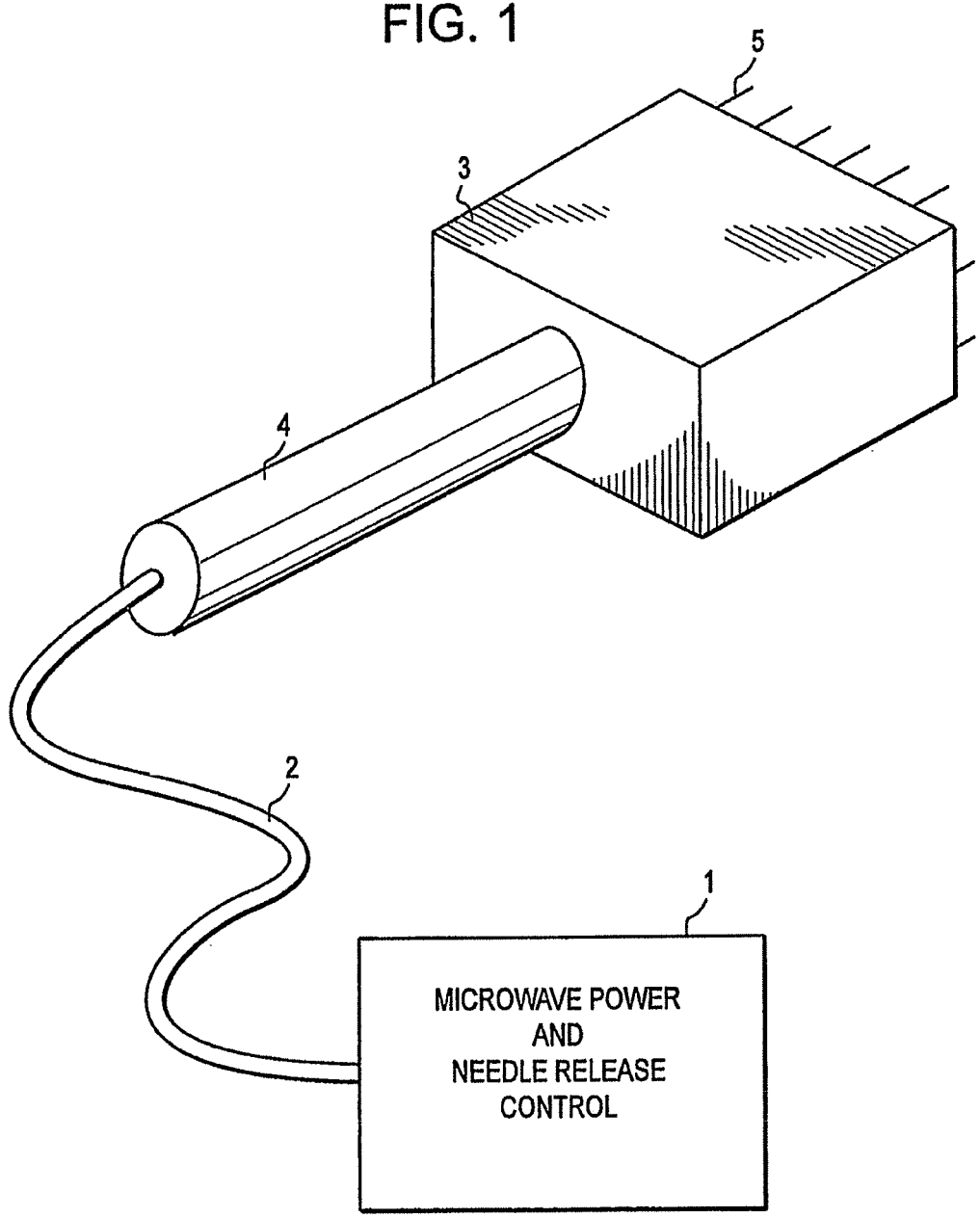
FIG. 1 is a schematic representation of an application in accordance with this invention.

Referring now to the drawings, a power and control unit (1) supplies up to 500 watts of microwave power via a coaxial cable (2) to a rectangular applicator (3). The head (3) has a handle (4) through which cable (2) passes, and an array (5) of retractable needles which are designed to provide precise irradiation of the tissue in the vicinity of the selected incision point. The unit (1) also contains a switching mechanism and control electronics to energize and release the array of needles.

As shown in FIGS. 2 and 3, the applicator head (3) includes a rectangular waveguide (6) around the periphery of which the needles of array (5) are located. The waveguide is a TM.sub.11 mode waveguide and is filled with a suitable dielectric. For irradiation of a region 5 cm long by 2 cm wide, the rectangular waveguide should have corresponding dimensions and may be filled with a medium whose dielectric constant (.epsilon..sub.K.) is about 50. These parameters dictate that the microwave operating frequency should be of the order of 1 GHz. The specific values given here are by of example only; it will be appreciated that a range of applicators designed to irradiate different volumes of tissue may be developed and these, of necessity, will have different dimensions and may require a different dielectric medium and a different operating frequency from that given above. In the illustrated embodiment, each of the needles is 3 cm long and made of steel. When the applicator is in operation, these needles will be advanced into the tissue where they function as an extension to the waveguide. A typical needle array may comprise about 20 needles. By employing a TM mode waveguide, leakage of energy through the "needle wall"—i.e., the area bounded by the array of needles—is kept to a low level (typically less than 10%).

FIG. 2 also shows a collar (8) to which each of the needles of the array (5) are secured. Collar (8) is acted upon by spring (9) which forms part of a solenoid mechanism (10) for controlling the advance and retraction of the array of needles. Power is supplied to the solenoid mechanism (10) via cable (11). As illustrated in FIG. 2, coaxial line (2) terminates within the dielectric-filled waveguide (6).

In operation, a surgeon will position the applicator head (3) against the region of tissue (e.g. liver) which is about to be incised. Initially the needle array (5) is retracted within head (3). When the applicator is actuated, solenoid mechanism (10) causes the needles of array (5) to be extended into the patient's tissue. Once they are embedded in the tissue, microwave energy at the desired frequency (e.g. 1 GHz) is supplied to waveguide (6) and passes therefrom into the volume of tissue enclosed by the array (5) of needles. Energy is supplied at a typical power level of 500 watts for a duration of about 15 secs when an applicator of the dimensions 5 cm.times.2 cm and a needle length of 3 cm is used. At the end of the treatment period, the microwave source is switched off and needle array (5) is retracted. The surgeon may then proceed with the incision and any subsequent procedures as may be necessary.

Blood loss from incision of tissue after heat treatment as described is greatly reduced in comparison to the results obtained in the absence of such heat treatment.

What is claimed is:

1. In the surgical treatment of a human or animal body, a method of severing a portion of diseased liver from the liver without excessive bleeding, the method comprising:
   providing a device, the device comprising an applicator having at least one face and including an array of four identical needles arranged in a rectangular pattern of two rows by two columns that define a central channel structured and arranged such that two of said four tissue-piercing needles are positioned on one side of a width of liver tissue 2 cm across or less, and two of said needles are arranged to be positioned on an opposite side of said width of diseased liver tissue 2 cm across or less said width of tissue defining a planned incision line corresponding with said channel, said plurality of four tissue-piercing needles structured and arranged to be energizeable together to deliver three-dimensional energy among and with a cross-flow across said plurality of identical tissue-piercing needles, said applicator structured to be operably coupled to a source of electromagnetic energy;
   positioning said array of four needles arranged in two rows by two columns such that two of said four tissue-piercing needles are positioned on one side of a width of liver tissue 2 cm across or less and two of said needles are positioned on an opposite side of said width of liver tissue 2 cm across or less such that said positioning defines a planned incision line corresponding with said channel, said array of needles serving to confine and transmit the electromagnetic energy field three-dimensionally;
   inserting the tissue-piercing distal tips of said array of needles from said at least one face of the applicator into said liver tissue at a point on the planned incision line such that said four needles define a volume of liver tissue to be treated;
   applying said electromagnetic energy three-dimensionally among said array of four needles into the volume of liver tissue at said point on the planned incision line such that localized heating of said volume of liver tissue is achieved and blood vessels within said volume of liver tissue are coagulated;
   removing the tissue-piercing distal tips of said array of needles from the volume of tissue to be treated;
   advancing the applicator along the planned incision line in step-wise manner, inserting the tissue-piercing distal tips of said array of needles into a subsequent volume of tissue to be treated along said planned incision line, and applying said electromagnetic energy three-dimensionally among said array of four needles into the volume of the tissue to be treated along said planned incision line until said electromagnetic energy has been applied along the length of said incision line and blood vessels in the liver tissue along said planned incision line are coagulated; and
   severing the diseased liver tissue from the liver by incision along said planned incision line without excessive bleeding.

2. The method as claimed in claim 1 further comprising applying electromagnetic energy to the volume of the tissue to be treated for a time sufficient to raise the temperature of the tissue or organ by 20 to 30° C.

3. The method as claimed in claim 1, wherein said array of needles includes at least one row of said array of needles.

4. The method as claimed in claim 1, wherein said needles are parallel with one another.

5. The method as claimed in claim 1, wherein said needles are straight.

6. The method of claim 1 wherein said source of microwave energy comprises a wave guide for microwave transmission to said array of needles.

7. A method of severing tissue from a human or animal body without excessive bleeding, the method comprising:
   (a) inserting a device into tissue or a part of an organ to be treated, the device comprising an applicator structured to be operably coupled to a source of electromagnetic energy, said applicator including an array of four needles arranged in a rectangular pattern of two by two needles thereon, each needle having tissue piercing means;
   (b) positioning the tissue-piercing means of said array of four needles into a desired depth of approximately 40 millimeters in a volume of the tissue to be treated defined by said four needles;
   (c) applying the electromagnetic energy to the desired depth of the volume of tissue to be treated to heat the tissue;
   (d) advancing the tissue-piercing means of said array of needles along the length of a planned incision line;
   (e) creating a heat-treated tissue volume as long as the length of the planned incision line, as deep from the surface as the desired depth, having a width that extends across the planned incision line between said needles arranged in said rectangular pattern of two by two needles, wherein the heat-treated tissue volume includes the planned incision line and further wherein blood vessels located within said tissue are coagulated to said desired depth;

(f) making an incision into the desired depth of the volume of tissue which has been heated along said planned incision line; and (g) severing the tissue or part of organ from the body by incision along said planned incision line without excessive bleeding.

8. The method as claimed in claim 7, in which the step of applying electromagnetic energy comprises heating said tissue by 20 to 30° C.

9. The method as claimed in claim 7, wherein said electromagnetic energy is provided at microwave frequency.

10. The method as claimed in claim 7, wherein said array includes at least one row of said needles.

11. The method as claimed in claim 7, wherein said array of needles is rectangular.

12. The method as claimed in claim 7, wherein said needles are the same length as one another.

13. The method as claimed in claim 7, wherein positioning the tissue-piercing means of said array of needles to the desired depth of the volume of the tissue to be treated further includes actuating said applicator to cause said tissue-piercing means of said array of needles to extend into said desired depth of the volume of tissue.

14. The method of claim 13 wherein extending the tissue-piercing means of said array of needles into a desired depth of a volume of the tissue to be treated further includes retracting said needles from said tissue.

15. A method of surgically severing tissue from a human or animal body without excessive bleeding, the method comprising:
(a) providing an applicator structured to be operably coupled to a source of electromagnetic energy, said applicator having an array of more than 3 identical needles thereon, each needle having a sharp tissue piercing end;
(b) selecting in a tissue volume a planned incision plane with a planned incision depth and containing tissue which is prone to substantial bleeding upon incision thereinto;
(c) at said planned incision plane, perforatingly inserting said sharp tissue-piercing ends of said needles to an identical planned insertion depth to pierce said tissue which is prone to bleeding;
(d) applying said electromagnetic energy via said needles to said tissue volume to coagulate tissue in a coagulation volume, said coagulation volume containing said planned incision plane, straddling said incision plane and extending to the planned incision depth, in order to convert tissue in said coagulated volume from tissue prone to bleeding upon incision thereinto into tissue resistant to bleeding upon incision thereinto; and
(e) making an incision to the planned incision depth along said planned incision plane to sever said tissue from the body without excessive bleeding.

16. A method as claimed in claim 15 which includes removing said needles from said coagulation volume before said step of making an incision.

17. A method as claimed in claim 15 which includes repeating steps (c) and (d) at a location advanced along said planned incision plane.

18. A method as claimed in claim 15 in which said perforatingly inserting said sharp tissue piercing ends to a planned incision depth comprises inserting a needle array of two by two needles such that two needles straddle either side of said planned incision plane, and in which the applying electromagnetic energy including applying said energy three dimensionally between needles across said planned incision plane.

19. A method as claimed in claim 15 in which the slice has a width of about 2 cm and is bisected by said planned incision plane.

20. A method as claimed in claim 15 which includes providing each needle of metal conducting material with a metal cylindrical conducting surface extending therealong, and in which said step of applying electromagnetic energy comprising providing a voltage to each needle so as to convert tissue into said coagulation volume by way of ablation energy transmitted into said tissue all of the way along said metal cylindrical conducting surfaces.

21. A method as claimed in claim 20 in which said step of applying electromagnetic energy comprising providing a voltage between needles in the array which are inserted into said tissue and located straddling the planned incision plane.

* * * * *